United States Patent [19]
Jeng et al.

[11] Patent Number: 6,067,463
[45] Date of Patent: May 23, 2000

[54] METHOD AND APPARATUS FOR NON-INVASIVELY MEASURING THE AMOUNT OF GLUCOSE IN BLOOD

[75] Inventors: Tzyy-Wen Jeng, Vernon Hills; Shu-Jen Yeh; John M. Lindberg, both of Grayslake, all of Ill.; Joseph Larry Pezzaniti, Madison, Ala.; Omar S. Khalil, Libertyville, Ill.; Gary M. Oosta, Gurnee, Ill.; Charles F. Hanna, Libertyville, Ill.; Arnold F. Stalder, Pleasant Prairie, Wis.; Ete Z. Szuts, Byfield, Mass.

[73] Assignee: Abbott Laboratories, Abbott Park, Ill.

[21] Appl. No.: 09/225,430

[22] Filed: Jan. 5, 1999

[51] Int. Cl.[7] .......................................................... A61B 5/00
[52] U.S. Cl. ........................... 600/336; 600/322; 600/310
[58] Field of Search ..................... 600/310, 316, 600/317, 322, 323, 326, 336, 473, 476

[56] References Cited

U.S. PATENT DOCUMENTS

| | | |
|---|---|---|
| 5,178,142 | 1/1993 | Harjunmaa . |
| 5,303,026 | 4/1994 | Strobl et al. ............................. 600/476 |
| 5,429,128 | 7/1995 | Cadell et al. . |
| 5,436,455 | 7/1995 | Rosenthal et al. . |
| 5,553,616 | 9/1996 | Ham et al. ............................... 600/316 |
| 5,645,060 | 7/1997 | Yorkey .................................... 600/323 |

FOREIGN PATENT DOCUMENTS 9316629  2/1993  WIPO .

*Primary Examiner*—Eric F. Winakur
*Attorney, Agent, or Firm*—David L. Weinstein

[57] ABSTRACT

A method and apparatus for measuring the concentration of an analyte of interest, e.g. glucose, in blood non-invasively, i.e., without penetrating the skin or obtaining a biological sample from the body of a patient. The method and apparatus uses a plurality of measurement channels with appropriate wavelengths of interest to control variations of signal and to separate the contribution of the analyte of interest from those of interfering compounds. The method and apparatus of this invention can also be adapted to allow a portion of a body part to be engorged with blood to bring about greater accuracy in optical measurements. In the method of this invention, at least two similar, but not identical, measurements are made concurrently. For example, at least two measurements can be made with similar, but not identical, wavelengths of electromagnetic radiation. The two wavelengths should not be overlapping to allow maximum non-identity. By making measurements concurrently, each measurement channel in the system experiences variations as they occur substantially simultaneously in all channels. By selecting one of the channels as a reference channel and by normalizing the optical measurements of the other channels to this reference channel, the variations common to all channels are eliminated. Removing these common variations from the optical measurements by normalization, such as by calculating ratios of the measurement of each of the measuring channels to that of the reference channel, will allow the actual changes of the signal for a specific analyte of interest to be measured.

21 Claims, 5 Drawing Sheets

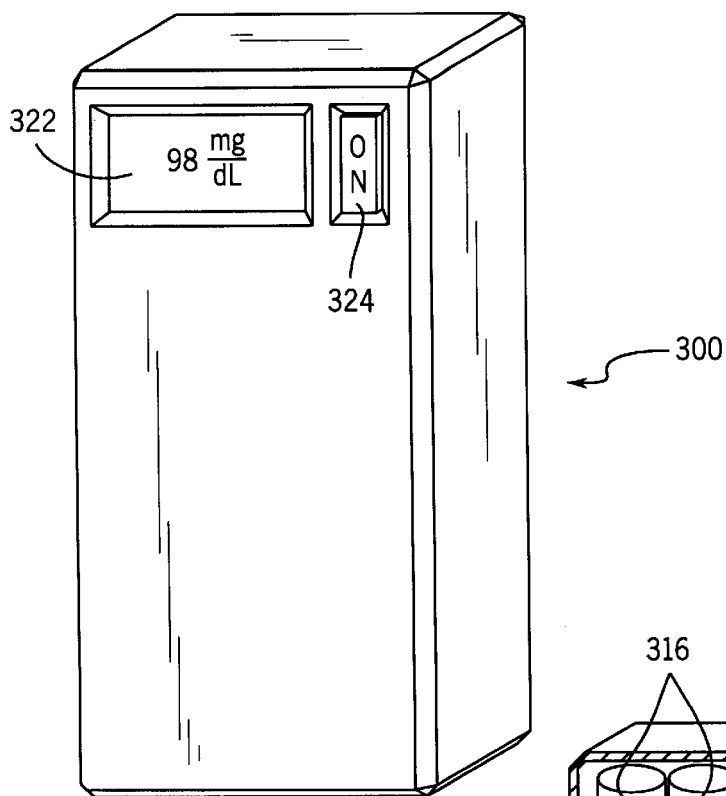
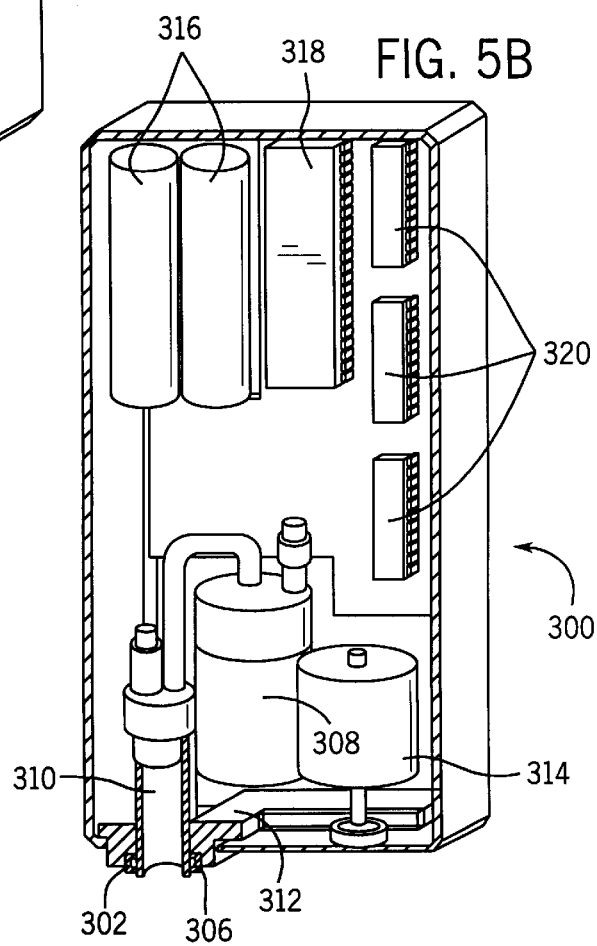

METHOD AND APPARATUS FOR NON-INVASIVELY MEASURING THE AMOUNT OF GLUCOSE IN BLOOD

BACKGROUND OF THE INVENTION

1. Field of the Invention

This invention relates to a method for non-invasively determining the concentration of an analyte of interest in a mammal, and, in particular, a method for non-invasively determining the concentration of glucose in blood.

2. Discussion of the Art

The prevalence of diabetes has been increasing markedly in the world. At this time, diagnosed diabetics represented about 3% of the population of the United States. It is believed that the total number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of obtaining blood from an individual by a variety of methods, such as by needle or lance. An individual then coats a paper or a plastic strip carrying chemistry with the blood obtained, and finally inserts the blood-coated strip into a blood glucose meter for the measurement of glucose concentration by determination of change in reflectance or electric signal of a biosensor.

Recently, new approaches have been pursued to measure the level of glucose in the blood stream non-invasively. These approaches use spectroscopic measurement through a body part with wavelengths in the near infrared region of the electromagnetic spectrum. However, due to both variations in the optical measurements and low signal strength of the optical readings taken through a body part, not one of the many disclosed methods has demonstrated sufficient precision for a commercial product.

Variations arise in the course of taking in vivo measurements of blood components through a body part for several reasons. Variations well known to those skilled in the art are primarily due to the interface between the body part and the measuring instrument, which is inconsistent. This interface can vary on account of motion of the body part, which results in a change in the degree of contact between the body part and the instrument. However, there are a host of natural variations within the body part that have not been addressed by the art. The natural variations could be of short term duration, such as those caused by variations in blood flow resulting from the heartbeat, fluctuations of oxygen saturation caused by breathing, changes in blood constituents caused by a meal, changes in hydration, changes in posture, and changes of diameter in blood vessels under parasympathetic nerve and endocrine control. Natural variations could also be of long term duration, such as those caused by variations in body weight, monthly menstruation cycle in women, or seasonal change in thyroid functions. Some of these variations have been suggested in the art in reference to calibration processes, while some of these variations have been ignored. It is also known to those skilled in the art that different optical readings will result if measurements are made on different locations of a body part. For example, a finger is neither homogeneous nor uniform in diameter. Performing multiple measurements through a finger with reinsertion of that finger into the instrument will inevitably bring about measurement from non-identical sites. Consequently, the results obtained at different times with different insertions of the finger into the instrument will exhibit variations reflecting one or more of these factors. These variations can be sufficiently large to mask weak signals related to fluctuation in the concentration of an analyte. When the variation resulting from these factors masks the weak signal of the analyte of interest, such as glucose, the results could be too imprecise for reliance by the patient.

The foregoing problems have been addressed in several ways. According to one technique, the data can be collected over a short period of time. This technique is based on the premise that if the period of time for data collection is short, variations should be small. However, this premise is inaccurate. In the situation where the signal is very weak, such as, for example, in the case of in vivo measurement of glucose, a short period of time for data collection results in a reduction in signal. Therefore, data quality would be poor on account of low statistical averaging over a short period of time for measurement. Furthermore, this technique can only account for those variations that happen at about the same frequency as the observation, such as the effect of heartbeat. This technique could not account for other variations, such as reinsertion error, blood vessel dilation, or variation of body part due to long-term body structure change, such as gain or loss of body weight.

According to a second technique, a spectrum having a wide wavelength range and a small band path and weighting factors among the different wavelengths is used to reduce noise associated with different wavelengths by averaging. This technique is based on the premise that over an appropriate period of time for collecting data, averaging could reduce noise, which is randomly occurring in frequency and in amplitude. However, spectrum collection is time-consuming and the variation due to noise in a biological system is not random.

According to a third technique, a physical constraint device is used in order to minimize motion of the body. There are several disadvantages associated with this technique. For example, only a limited number of body locations could be fitted into the device to minimize variation resulting from motion and other causes. Squeezing a body part sufficiently to stop the heart pulse is not acceptable for certain parts of the body. In addition, motion and other naturally occurring rhythms can be halted only for a short period of time, for the reason that there must be circulation of blood to prevent damage to the body part. Moreover, there would have to be many different sizes of the restraining device to account for the many different sizes of body parts in the population. Finally, the effectiveness of constraining devices is not great because the devices are prone to human error, and variations other than motion and repositioning could not be addressed. For example, U.S. Pat. No. 5,178,142 discloses an apparatus and a method for using a tunable laser to form an optical bridge to measure the glucose level non-invasively through a preferred site of body, the earlobe. This optical bridge has a measuring wavelength at about 1600 nm and a shorter reference wavelength. The difference of the intensity of the transmitted light of the measuring wavelength to that of the reference wavelength was adjusted to be close to zero by tuning the wavelength of the reference wavelength while viewing a compressed earlobe. The earlobe was then relaxed from compression and the difference of intensity of the transmitted light at the measuring wavelength to that of the tuned reference wavelength was taken. This measurement would represent a difference of transmittance of the relaxed earlobe with normal blood content over the compressed earlobe with reduced blood content. Reducing the blood content of the earlobe by compression is difficult to achieve and painful to the patient. The other difficulty in practicing this method is in controlling the measurement when the earlobe is relaxed. It is difficult to obtain reproducible and meaningful optical readings because it is difficult to maintain proper contact between the optical elements and the earlobe without some degree of compression. Thus, there are degrees of compression of the earlobe in the measurement in the relaxed state, but these degrees of compression are uncertain. That uncertainty is directly translated into the variability of the measurement, thereby further causing imprecision in the determination of the level of glucose in the blood stream.

U.S. Pat. No. 5,429,128 discloses a finger receptacle to minimize motion of the finger during recording of spectroscopic signals for determination of level of glucose in the blood stream non-invasively. This device includes a spring-mounted roller to hold the finger in position. The difficulty in using this device results from the strength of the spring. When the spring is too strong, it compresses the finger, causing discomfort and reduction of blood content in the finger. When the spring is not strong enough to hold the finger immobile, the motion of the finger interferes with the optical reading. That variability is directly translated into the variability of the measurement, thereby further causing imprecision in the determination of the level of glucose in the blood stream.

U.S. Pat. No. 5,436,455 discloses a removable finger insert to facilitate fitting an individual's finger into the optical system. The removable finger insert can be one of a set of inserts of different sizes, whereby the user can choose the one providing the best fit. This device significantly reduces the problem encountered in U.S. Pat. No. 5,429,128 but encounters other difficulties. A person's finger is not necessarily constant in size all the time. For example, a finger could be smaller in the morning than in the afternoon, like a person's foot, which is smaller in the morning than in the afternoon. This change of size is likely due to the upright posture that allows more blood to stay in the extremities at the later part of the day, thereby enlarging their size. Furthermore, a person may not fit the finger insert the same way all the time. These variations are directly translated into the variability of the measurement, thereby further causing imprecision in the determination of the level of glucose in the blood stream.

In addition to the problem of variations in making an optical measurement through a body part to determine the level of glucose in the blood stream non-invasively, there are the problems of low volume of sample and low signal strength. The blood content in a body part such as a finger is about 3 to 5% of the volume of that body part, depending on race, individual, site of measurement, and physiological state. The signal of interest, e.g., the level of glucose in the blood stream, is provided by this small volume fraction, yet the majority of the signal from the rest of the volume in an optical measurement is of an interfering nature. U.S. Pat. No. 5,178,142 addressed this problem by using the difference of two optical measurements of a body part. One measurement is taken under normal conditions, with the blood remaining in the body part, and the other measurement is taken with the blood squeezed out of the body part. This method could result in several difficulties:

1) The method of U.S. Pat. No. 5,178,142 requires extreme squeezing in order to squeeze all of the blood from a body part. There are only a limited number of body parts, such as an earlobe or a web between a thumb and its neighboring index finger, that would be suitable for this type of squeezing.

2) To achieve the desired amount of squeezing is painful to the patient.

3) A recovery time is needed for the body part to return to its natural state before a repeat measurement can be attempted.

4) It is difficult to ascertain whether all the blood has been squeezed out in one measurement and the full amount has been left in another measurement.

This method is also disadvantageous when compared with a method where blood content for the observation can be increased to provide a more specific signal in the presence of a vast amount of background signal from blood-free tissue.

It is therefore desirable to provide a method to reduce or account for the variability of an optical reading through a body part, preferably engorged with blood, to provide adequate precision for non-invasive determination of an analyte of interest in vivo. At the same time it is desired that the method eliminate the discomfort and side effects previously discussed.

SUMMARY OF THE INVENTION

This invention provides a method and apparatus for measuring the concentration of an analyte of interest, e.g. glucose, in blood non-invasively, i.e., without penetrating the skin or obtaining a biological sample from the body of a patient. The method and apparatus uses a plurality of measurement channels with appropriate wavelengths of interest to control variations of signal and to separate the contribution of the analyte of interest from those of interfering compounds. The method and apparatus of this invention can also be adapted to allow a portion of a body part to be engorged with blood to bring about greater accuracy in optical measurements.

In the method of this invention, at least two similar, but not identical, measurements are made concurrently. For example, at least two measurements can be made with similar, but not identical, wavelengths of electromagnetic radiation. The two wavelengths should not be overlapping to allow maximum non-identity. Each one of the optical measurements is carried out in a given channel. For each channel, a source of light, a body-instrument interface, a body part as measurement site, and a detector are required. Concurrent measurements in each channel are essential. As used herein, concurrent measurements refer to making at least two measurements of electromagnetic radiation at substantially the same time on substantially the same body part with substantially the same optical arrangement. By making measurements concurrently, each channel in the system experiences variations as they occur substantially simultaneously in all channels. These variations, which are designated "common noise", could include variations in measurement hardware, such as power source fluctuation or lamp drift; ambient temperature change; and other variations, such as change in body-instrument interface or change in body part. By selecting one of the channels as a reference channel and by normalizing the optical measurements of the other channels to this reference channel, the variations common to all channels are eliminated. Removing these common variations from the optical measurements by normalization, such as by calculating ratios of the measurement of each of the measuring channels to that of the reference channel, will allow the actual changes of the signal for a specific analyte of interest to be measured. Because of the simplicity in normalizing measurements, the measurement operation can be carried out very fast. With high-speed electronics under control of a microprocessor, the in vivo non-invasive determination of blood glucose or other analyte of interest can be made almost instantly.

This invention overcomes the problem of variation normally occurring in the non-invasive in vivo measurement of glucose or other analyte of interest through a body part. With the immediate and rapid operating characteristics of this invention, it is possible to even further improve signal quality by averaging additional measurements over an extended period of time. The invention is also convenient to the user because of the elimination of a constraining device. Because the user does not have to insert his body part into a constraining device, he is unlikely to use the constraint device incorrectly. Adding a channel as a reference in a multiple-channel instrument is more cost-effective than building an elaborate constraining device. This is particularly true if a constraining device requires moving parts or a power source for operation. The apparatus is versatile in that it can be used in a transmittance measurement mode as well as in a reflectance measurement mode. This invention reduces variations in measurements of concentration of an analyte of interest, especially when the reference channel is selected optimally.

BRIEF DESCRIPTION OF THE DRAWINGS

FIGS. 5A, 5B, and 5C are schematic diagrams illustrating one embodiment for practicing this invention. These diagrams show the integration of a vacuum generating device for blood engorgement with the observation site of the inner side of a forearm. FIG. 5A is a front elevational view of a handheld instrument. FIG. 5B is a cut-away view showing the essential elements in this instrument. FIG. 5C is an enlarged view showing an optical measurement, wherein tissue is drawn into the tube by means of low pressure brought about by vacuum.

DETAILED DESCRIPTION

As used herein, the term "channel" means a specified frequency band for transmitting and receiving electromagnetic signals. The expression "coefficient of variation", abbreviated as CV, means the value, expressed in percentage, of standard deviation divided by the mean. The terms "mean" and "average" are equivalent and are used interchangeably. The term "concurrent" refers to a mode of measurement in which at least two measurements of electromagnetic radiation are made. Two measurements are concurrent if they are made at substantially the same time on substantially the same body part with substantially the same optical arrangement.

Figure 1:
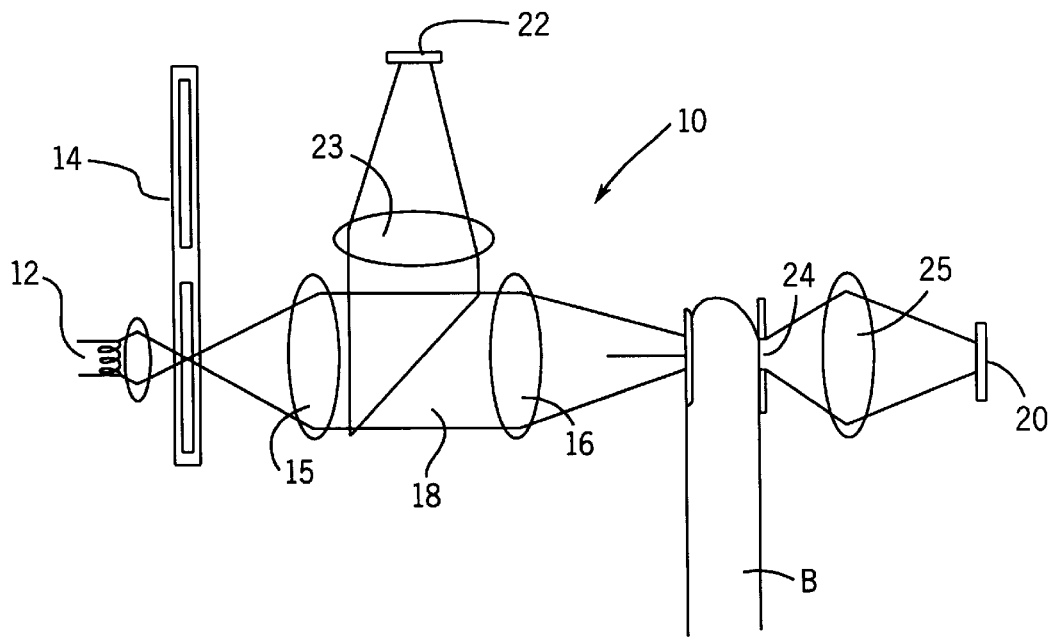
FIG. 1 is a schematic diagram illustrating one embodiment for practicing this invention.

Referring now to FIG. 1, a filter photometer unit 10 includes a source of light 12 having a band-pass filter set 14 and a lens system 15 for collimating light from the filter set 14 and a lens system 16 for focusing light onto a body part "B". The band-pass filter set 14 selects one desired wavelength at a time by rotating the set to place a given filter in the path of the beam. The rate of rotation should be sufficiently high (e.g., greater than 500 Hz) to achieve the concurrency requirement, i.e., observing with substantially the same optical arrangement at substantially the same time on substantially the same observation area of the body part. Before light reaches the body part, a beam splitter 18 separates the beam into two portions. The major portion is directed toward the body part and ultimately reaches a detector 20. The minor portion is directed toward a detector 22. The channel associated with this detector 22 can be used to monitor the stability of the source of light 12 and can be used to correct for light source drift if lamp intensity drift occurs. A lens system 23 is used to focus the light from the beam splitter onto the detector 22.

The body part, e.g., a finger, earlobe, is positioned at the place where the beam from the source of light is focused. Light passing through the body part is transmitted through an aperture 24 and then through a lens system 25 to deliver light to the detector 20. The detector 20 is connected to a data amplification unit having a pre-amplifier (not shown) and an amplifier (not shown). Amplified readings are transferred through connecting cables to a computer. The computer controls the software operation for collecting data and storing measurement readings as a data file. The data amplification unit, the cable connecting the amplification unit to the control computer, the control computer itself, and the display device are not shown in this figure for the sake of clarity.

Figure 2:
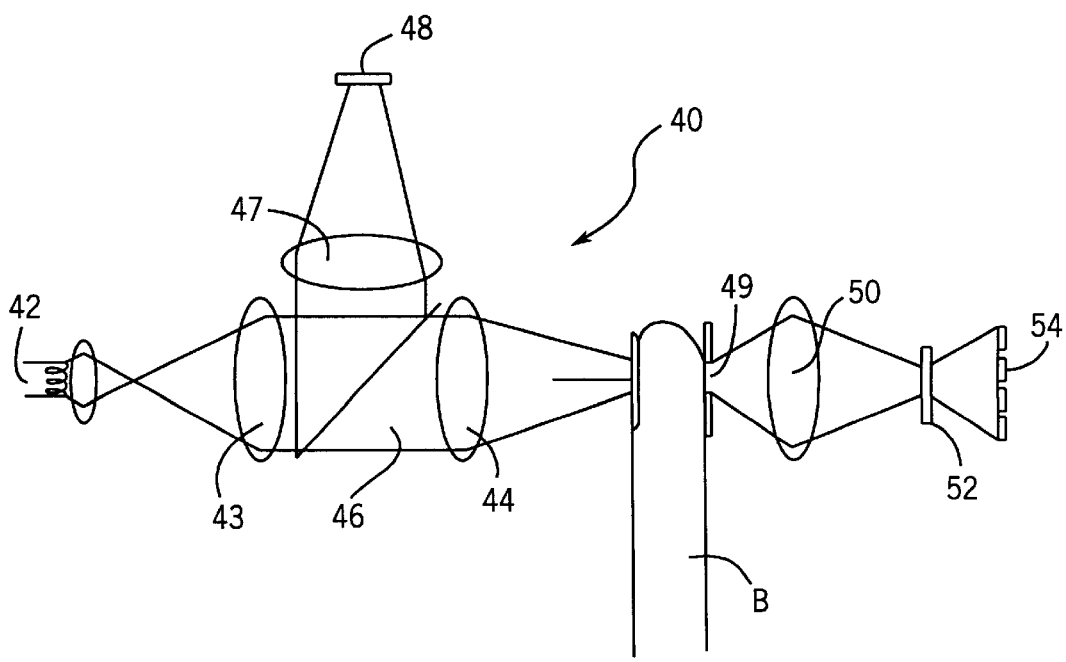
FIG. 2 is a schematic diagram illustrating another embodiment for practicing this invention.

Another embodiment is shown in FIG. 2. Referring now to FIG. 2, a filter photometer unit 40 includes a source of light 42 and a lens system 43 for collimating light from the source of light 42 and a lens system 44 for focusing light onto a body part. Before light reaches the body part, a beam splitter 46, from whence that portion is transmitted to a detector 48, separates a portion of the source beam. The channel encompassed by this detector 48 can be used to monitor the stability of the source of light 42 and can be used to correct for light source drift if lamp intensity drift occurs. A lens system 47 is used to focus the light from the beam splitter onto the detector 48.

The body part, e.g., a finger, earlobe, is positioned at the place where the beam from the source of light is focused. Light passing through the body part "B" is transmitted through an aperture 49 and then through a lens system 50 to deliver light to a dispersive element 52. A segment of the spectrum is delivered to a detection element of an array detector 54. The dispersive element, which separates broad band light into segments of different wavelengths, could be either a prism or a diffraction grating. Detector 48 and detector 54 are connected to a data amplification unit having a pre-amplifier (not shown) and an amplifier (not shown).

Amplified readings are transferred through connecting cables to a computer. The computer controls the software operation for collecting data and storing measurement readings as a data file.

The data amplification unit, the cable connecting the amplification unit to the control computer, the control computer itself, and the display device are not shown in this figure for the sake of clarity.

This invention, which is characterized by a plurality of channels, reduces the variation in data, thereby improving the reproducibility of data. Variations arising from bodily changes and body-instrument interface changes are shared in a plurality of channels substantially simultaneously. Due to the concurrency of this optical system, the measurements made in each of the channels are related to those made in the other channels with respect to using substantially the same optical system to observed substantially the same body part at substantially the same time. The wavelength of any given channel should not be overlapping with the wavelength of any other channel to allow maximum differentiation to ensure greater specificity. By designating an appropriate channel as a reference channel and then calculating the ratio of the output of each measurement channel to the output of the reference channel, the changes that are common in the measurement channels can be reduced or minimized. For example, in a simplified situation, it can be assumed that two channels, channel A and channel B, are present. It can be further assumed that the measurement made in channel A has the mean value $X_a$ and that the measurement made in channel B has the mean value $X_b$. The standard deviation of the measurements in channel A is $S_a$ and the standard deviation of the measurements in channel B is $S_b$. Accordingly, the coefficient of variation (CV) in channel A, i.e., $CV_a$, is equal to $S_a/X_a \times 100\%$ and the coefficient of variation in channel B, i.e., $CV_b$, is equal to $S_b/X_b \times 100\%$. These values of CV, $CV_a$ for channel A and $CV_b$ for channel B, could be very high on account of such factors as motion, heartbeats, or re-insertion variations of the body part. When the data is processed by using channel A as the measurement channel and channel B as the reference channel, the mean value of this ratio can be expressed as R, and it is equal to $X_a/X_b$. The standard deviation of R, which may be designated $S_R$, would be much smaller than either Sa or $S_b$. The CV of R, i.e., $CV_R = S_R/R \times 100\%$, would be significantly smaller than either $CV_a$ or $CV_b$. The statement that $CV_R$ would be significantly smaller than either $CV_a$ or $CV_b$ is true when the variation of channel A and the variation of channel B are related to and are synchronous with each other. In other words, the features of variation in the two channels must be common. This condition can be met by requiring concurrent observation. For further clarification of this concept, a simulation is shown below. In this simulation, three scenarios (Scenario A, Scenario B, and Scenario C) are compared.

Scenario A, shown in Table 1 below, is a simulation of a situation wherein the background measurement is fixed at a constant value. This scenario simulates an in vitro measurement through a cuvette, where background could remain constant. An arbitrary value of 100 is given to the background reading to represent the optical reading through a cuvette. It is assumed that an optical system having two channels for measuring an analyte of interest inside the cuvette is set up. This analyte would contribute some values for reading in channel A (e.g., value of 10) and some values in channel B (e.g., value of 15). Random noise in each of the channels is generated by a random number generator such as the RAND( ) function in an Excel spreadsheet. The observed value of the reading in each channel is the sum of the reading contributed by the background, the reading contributed by the analyte of interest, and the reading contributed by random noise. The reading contributed by random noise is expressed as a fraction of the reading contributed by the analyte of interest The equation (1) below is the formula for the calculation of the observed optical reading in each channel.

$$\text{Observed reading} = \text{Background reading} + [\text{Analyte reading} \times (1+ \text{variation})] \quad (1)$$

Standard statistical methods are then used to analyze the results of the 10 simulated data points for the two channels and for using the ratio of the readings of channel A to those of channel B. The CV value in channel A is 2.7%. The CV value in Channel B is 5.3%. The CV for the ratio of the reading of channel A to the reading of Channel B is 6.2%.

There is no significant difference in CV values. Therefore, the observation of a single channel would be sufficient when there is no significant variation in background. This scenario indicates why the instruments used in the in vitro measurements need not use ratios of measurements of optical readings of channels.

TABLE 1

| | Scenario A: Constant Background | | | | | | | | |
|---|---|---|---|---|---|---|---|---|---|
| | Background reading in channel | | Analyte reading in channel | | Random variation in channel (%) | | Observed reading in channel | | Ratio |
| Observation | A | B | A | B | A | B | A | B | A/B |
| 1 | 100.0 | 100.0 | 10 | 15 | 0.29 | 0.63 | 112.9 | 124.5 | 0.91 |
| 2 | 100.0 | 100.0 | 10 | 15 | 0.40 | −0.30 | 114.0 | 110.4 | 1.03 |
| 3 | 100.0 | 100.0 | 10 | 15 | −0.34 | −0.35 | 106.6 | 109.7 | 0.97 |
| 4 | 100.0 | 100.0 | 10 | 15 | 0.05 | −0.34 | 110.5 | 110.0 | 1.00 |
| 5 | 100.0 | 100.0 | 10 | 15 | −0.07 | 0.62 | 109.3 | 124.3 | 0.88 |
| 6 | 100.0 | 100.0 | 10 | 15 | −0.07 | −0.30 | 109.3 | 110.5 | 0.99 |

TABLE 1-continued

Scenario A: Constant Background

| | Background reading in channel | | Analyte reading in channel | | Random variation in channel (%) | | Observed reading in channel | | Ratio |
|---|---|---|---|---|---|---|---|---|---|
| Observation | A | B | A | B | A | B | A | B | A/B |
| 7 | 100.0 | 100.0 | 10 | 15 | 0.16 | −0.19 | 111.6 | 112.2 | 0.99 |
| 8 | 100.0 | 100.0 | 10 | 15 | −0.43 | 0.15 | 105.7 | 117.3 | 0.90 |
| 9 | 100.0 | 100.0 | 10 | 15 | −0.30 | 0.38 | 107.0 | 120.7 | 0.89 |
| 10 | 100.0 | 100.0 | 10 | 15 | 0.32 | −0.31 | 113.2 | 110.3 | 1.03 |
| Mean | 100.0 | 100.0 | | | 0.00 | 0.00 | 110.0 | 115.0 | 0.96 |
| Std. Dev. | 0.0 | 0.0 | | | 0.29 | 0.41 | 2.9 | 6.1 | 0.06 |
| CV (%) | 0.0 | 0.0 | | | | | 2.7 | 5.3 | 6.2 |

Scenario B, which is shown in Table 2 below, simulates a situation where the background measurements of the two channels are independent and variable. In this simulation, concurrency has not been achieved. This situation could result from electronics not having sufficient speed for proper temporal concurrency or optics not being properly aligned to achieve spatial concurrency. In these cases channel A and channel B could be recording data at different times, and consequently, be affected by different phases of the heartbeat cycle. Instead of a constant arbitrary value of 100 for the background reading in scenario A, the background reading is randomly fluctuated with a standard deviation of 25 arbitrary units to represent the optical reading of tissue. Other simulated readings, such as those for the contribution from the analyte and from random noise, are the same as those in scenario A. The statistics are analyzed in a manner similar to that in the case of scenario A. The CV value of channel A and the CV value of channel B are significantly larger than those calculated in scenario A. The CV value for the ratio of the measurement of channel A to that of channel B is 47.8%, which is greater than that of either channel A (28.9%) or channel B (28.4%). This simulation illustrates that results can be made worse if the measurement arrangement is improper.

TABLE 2

Scenario B: Varying and Independent Background

| | Background reading in channel | | Analyte reading in channel | | Random variation in channel (%) | | Observed reading in channel | | Ratio |
|---|---|---|---|---|---|---|---|---|---|
| Observation | A | B | A | B | A | B | A | B | A/B |
| 1 | 100.0 | 95.0 | 10 | 15 | 0.29 | 0.63 | 112.9 | 104.5 | 1.08 |
| 2 | 130.0 | 77.0 | 10 | 15 | 0.40 | −0.30 | 134.0 | 72.4 | 1.85 |
| 3 | 125.0 | 128.0 | 10 | 15 | −0.34 | −0.35 | 121.6 | 122.7 | 0.99 |
| 4 | 80.0 | 145.0 | 10 | 15 | 0.05 | −0.34 | 80.5 | 140.0 | 0.57 |
| 5 | 70.0 | 101.0 | 10 | 15 | −0.07 | 0.62 | 69.3 | 110.3 | 0.63 |
| 6 | 113.0 | 68.0 | 10 | 15 | −0.07 | −0.30 | 112.3 | 63.5 | 1.77 |
| 7 | 99.0 | 60.0 | 10 | 15 | 0.16 | −0.19 | 100.6 | 57.2 | 1.76 |
| 8 | 65.0 | 75.0 | 10 | 15 | −0.43 | 0.15 | 60.7 | 77.3 | 0.79 |
| 9 | 57.0 | 105.0 | 10 | 15 | −0.30 | 0.38 | 54.0 | 110.7 | 0.49 |
| 10 | 89.0 | 100.0 | 10 | 15 | 0.32 | −0.31 | 92.2 | 95.3 | 0.97 |
| Mean | 92.8 | 95.4 | | | 0.00 | 0.00 | 93.8 | 95.4 | 1.09 |
| Std. Dev. | 25.1 | 26.7 | | | 0.29 | 0.41 | 27.1 | 27.1 | 0.52 |
| CV (%) | 27.1 | 28.0 | | | | | 28.9 | 28.4 | 47.8 |

Scenario C, which is shown in Table 3 below, simulates a situation where the background measurement is variable. Furthermore, the background readings of the two channels are closely related in sharing common variations because the two channels are concurrent. This simulation demonstrates the proper arrangement for the practice of this invention for in vivo measurement. Instead of random fluctuations of background readings for channel A and channel B that are unrelated to each other, the background reading of channel B is the same as that of channel A. Other simulated readings such as those for the contribution from the analyte and from random noise are the same as those encountered in scenario A. The statistics of this scenario are analyzed in a manner similar to that in the case of scenario A. The CV value of channel A and the CV value of channel B are similar to those in scenario B. However, the CV for the ratio of the measurement of channel A to that of channel B is 8.7%, which is much smaller than that of either channel A (28.9%) or channel B (24%). This simulation illustrates that less variability can be achieved when applying this invention to make the measurement concurrently.

TABLE 3

Scenario C: Varying But Common Background

| Observation | Background in channel A | Background in channel B | Analyte reading in channel A | Analyte reading in channel B | Random variation in channel A | Random variation in channel B | Observed reading in channel A | Observed reading in channel B | Ratio A/B |
|---|---|---|---|---|---|---|---|---|---|
| 1 | 100.0 | 100.0 | 10 | 15 | 0.29 | 0.63 | 112.9 | 109.5 | 1.03 |
| 2 | 130.0 | 130.0 | 10 | 15 | 0.40 | −0.30 | 134.0 | 125.4 | 1.07 |
| 3 | 125.0 | 125.0 | 10 | 15 | −0.34 | −0.35 | 121.6 | 119.7 | 1.02 |
| 4 | 80.0 | 80.0 | 10 | 15 | 0.05 | −0.34 | 80.5 | 75.0 | 1.07 |
| 5 | 70.0 | 70.0 | 10 | 15 | −0.07 | 0.62 | 69.3 | 79.3 | 0.87 |
| 6 | 113.0 | 113.0 | 10 | 15 | −0.07 | −0.30 | 112.3 | 108.5 | 1.03 |
| 7 | 99.0 | 99.0 | 10 | 15 | 0.16 | −0.19 | 100.6 | 96.2 | 1.05 |
| 8 | 65.0 | 65.0 | 10 | 15 | −0.43 | 0.15 | 60.7 | 67.3 | 0.90 |
| 9 | 57.0 | 57.0 | 10 | 15 | −0.30 | 0.38 | 54.0 | 62.7 | 0.86 |
| 10 | 89.0 | 89.0 | 10 | 15 | 0.32 | −0.31 | 92.2 | 84.3 | 1.09 |
| Mean | 92.8 | 92.8 | | | 0.00 | 0.00 | 93.8 | 92.8 | 1.00 |
| Std. Dev. | 25.1 | 25.1 | | | 0.29 | 0.41 | 27.1 | 22.3 | 0.09 |
| CV (%) | 27.1 | 27.1 | | | | | 28.9 | 24.0 | 8.7 |

Scenario C demonstrates the advantage of using the ratio of the signal of the measuring channel to the signal of the reference channel in reducing variation in an in vivo situation. The use of this ratio is based on the observation that the dominant factor in biological variation is shared among the channels when the channels are properly set up for concurrent observation. The requirement for concurrent observation is less stringent than that for congruent, i.e., overlapping, observation. In the conventional case of congruency, observations are made on different channels with some overlapping wavelengths on the same optical arrangement at exactly the same time on an identical sample. A set of beam splitters is usually used to meet the strict requirement of simultaneous observation with overlapping wavelengths. One of the drawbacks for achieving congruent observation by using a set of beam splitters is that the intensity of the light reaching the detector is significantly reduced. For example, a two-way beam splitter that splits light equally into two detectors will reduce the intensity of light in the beam to no more than 50% of that obtained without the beam splitter for each of the detectors of the two channels. A four-way beam splitter will reduce the intensity of light in the beam to no more than 25% of that obtained without the beam splitter for each of the detectors of the four channels. To enable more light to reach the detectors, the intensity of light from the source of light could be increased. However, increasing intensity of light leads to another drawback of this approach. That drawback is the tolerance level for the amount of energy entering a body part during an observation. The body part will have to tolerate four times as much energy input as it would without a beam splitter when a four-way beam splitter is used. A high amount of energy entering a body site could cause physiological responses, such as redness or pain, and could interfere with the optical recording. The design shown in FIG. 1 avoids these problems by allowing only light having the desired wavelength to pass through a filter to enter the body part. The band-pass filter absorbs light having undesired wavelengths. A rotating filter wheel is used to house various band-pass filters. By placing a given band-pass filter into the optical path, a channel having a given wavelength is formed. The data is therefore collected sequentially, with a different filter on the rotating wheel inserted into the optical path. Because of the single filter at one time nature of this filter wheel arrangement, readings from different channels are taken sequentially, and are, therefore, by definition not temporally congruent. However, with a detector employing high-speed electronics and a filter wheel having a high rotation speed, the time difference between channels can be minimized to the extent that a substantial equivalence in recording time can be reached to fulfill the concurrency requirement.

A method has been developed to determine concurrency. Measurements through a fingertip were collected with a four-channel recording instrument as shown in FIG. 1. The time offset of each channel is 2 ms; thus, the total time lapse is 8 ms for the sequence of the four channels. For clarity in the figure, the recorded data was processed by subtracting the value corresponding to the first data point in a given channel from the values corresponding to the remaining data points of that channel. Offset values were added to the differences so obtained so that results could be displayed in FIG. 3 without masking each other. The offset values were 0.5, 0.3, 0.2, and 0.1 for channels A, B, C, and D, respectively. In this figure, the peak value and valley value of each pulse for each channel appears at about the same data point number, thereby suggesting a high degree of concurrency. For further verification of concurrency, a correlation function was evaluated. In this evaluation method, the first pulse in channel A was selected as a reference segment. This pulse included data points starting from the first minimum and ending at the second minimum of the data curve of channel A. Then, starting from the first data point of channel A, a segment of data having the same number of data points as that of the reference segment was used as a test segment. The correlation coefficient for the test segment and the reference segment was calculated, and its value was assigned to the first data point of the correlation function. This process was repeated many times in a moving window fashion; in each repetition, one data point in the test segment was shifted along the data string of channel A. The last data point of the correlation was reached when the test segment included the last data point of the measurement in channel A. This process produced a correlation function with highest value located at the beginning of the reference segment, i.e., the first minimum. By means of the same process, that same reference segment in channel A was used to calculate the correlation coefficients for the other three channels. The portion of the correlation function calculated around the first pulse of data is shown in FIG. 4. By displaying only a portion of the entire function, higher resolution and minute variations can be visualized in FIG. 4. In FIG. 4, it can be seen that all four channels showed the same peak and valley positions. This observation suggests that the rate of collecting data was fast enough to allow common features in the measurement to appear at or near the same data point number for all four channels. Thus, concurrency among the four channels is indicated. The similar high values of correlation coefficient (1.00, 1.00, 0.99 and 0.98 for channels A, B, C, and D, respectively) are also indicative of a high degree of concurrency. When the time offset was increased to 4 ms per channel in another test, the correlation coefficients obtained were 1.00, 0.99, 0.98, 0.97 for channels A, B, C, and D, respectively. A correlation coefficient of greater than 0.9 is indicative of a high degree of concurrency while a correlation coefficient of greater than 0.5 indicates a sufficient degree of concurrency.

The correlation function can also be used to improve the relationship of data from different channels. If the peaks of different channels in the correlation function are at slightly different positions, the differences in peak positions in the correlation function can be used to shift data, by the number of data points that the peaks are offset from the peaks of a reference channel. This process, in effect, involves aligning data from different channels to the reference channel to have the best possible time correlation in the data. After such alignment, the data of the measurement channel is equivalent to having been time-shifted to have the same time of measurement as the data of the reference channel. It would then be most appropriate to use the aligned data rather than the original data for the normalization needed to reduce common noise.

The choice of a proper reference channel is critical and is further addressed here. A reference channel should show less variation than the measuring channel(s) arising from the analyte of interest, while in other aspects, the reference channel can exhibit variations similar to that of the measuring channel(s), so that concurrency can be maximized. The sensitivity of the reference channel to interference from the major constituents in the biological sample should also be considered. Several major components in a biological sample, e.g., proteins, lipids, blood cells, can change independently or as a function of the change in concentration of a given analyte, e.g., glucose. Therefore, any method for determining the concentration of a given analyte must be capable of determining not only the concentrations of major interfering components but also the effects of these interfering compounds on critical measurement parameters in order to provide an accurate result.

In this invention, at least one channel must be a reference channel and at least one channel must be measuring channel. Additional channels can allow a more precise determination of concentration of analyte by accounting for the co-existing interfering components in vivo. Theoretically, the maximum number of channels is not limited. However, only the major components need to be considered in a practical situation. In all cases in which a plurality of channels are used to practice this invention, the reference channel should have a wavelength different from that of the analyte of interest and those of the major interfering components. For this invention, the optimal number of channels preferably ranges from four to eight. In the situation of measuring the concentration of glucose, the major factors that interfere with the measurement include temperature and hemoglobin. Therefore, three measuring channels and one reference channel are capable of performing reasonably accurate measurements. However, in order to enhance precision in measuring concentration of glucose, additional channels for measuring water, lipids, salt, and protein are desirable. Accordingly, it is preferred to employ seven measurement channels and one reference channel for glucose measurements. A reference channel having a wavelength at about 900 nm appears appropriate.

The most preferred wavelengths to use for this invention are in the near infrared region of the electromagnetic spectrum. Visible light does not penetrate deeply enough into the tissue for suitable measurements. The skin and other tissue absorb radiation from the far infrared region of the spectrum very quickly, and, consequently, detection of transmitted or reflected light is difficult. The preferred wavelengths of radiation for this invention ranges from about 750 nm to about 2500 nm. Analytes of interest whose concentrations can be determined by this invention include, but are not limited to, glucose, urea, creatinine, ketone, bilirubin, hemoglobin, urobilinogen, and protein.

Another major difficulty with in vivo measurement of an analyte of interest is that only a small fraction of any given body part contributes to the signal. The blood content of most of the accessible body parts is about 3 to 5%. The remaining 95 to 97% of the body part either do not contribute to the signal or interferes with the signal. For example, adipose tissue, which has a high content of fat, would not contribute to the measurement of blood glucose, while bone, cartilage, tendon, and muscle interfere with the signal due to their special optical properties. Selecting a body part that is low in content of muscle, tendon, or bone is beneficial to the in vivo measurement. Body parts such as the earlobe, the web between thumb and index finger, or a fingertip are therefore the preferred sites mentioned in the prior art. However, all these sites have the drawback that blood content is low and highly variable. Earlobes' turning red or white, indicating different perfusion level of blood is often observed in an embarrassed or frightened individual. To a lesser degree and thus not as noticeable to the operator making the measurement, the blood content is affected by the size of blood vessel feeding the body part. The diameter of a blood vessel is controlled by the parasympathetic nerve and endocrine system, and thus could vary very rapidly. A method for increasing the volume of blood in the accessible area and also for minimizing its variation is therefore highly desirable. In this invention, a local area is preferably engorged with more blood for more sensitivity and more precise in vivo measurements. One of the techniques for increasing the blood content locally involves increasing the temperature. When a body part is heated, a regulatory mechanism called thermal stasis will operate to maintain body temperature by dilating blood vessels at the heated site to enhance blood flow to remove excess heat. A heating element with thermostatic control can be used to provide sufficient heat within the human comfort range to the local area to achieve this goal. In another technique, a vacuuming device could be fitted to the optical measurement device so that the site being interrogated could be maintained under a low pressure. Under reduced pressure by low level of vacuum, more blood will flow into the evacuated area. A low power vacuum pump, a suction cup with a spring-loaded plunger, or a mechanical device similar to a syringe can be used for this purpose. A low vacuum, e.g., 250 to 300 Torr, around a skin area having a diameter of 10 cm is enough to raise the surface of the skin about 3 mm above surrounding tissue in about 5 seconds. The engorgement of blood is evident from the red color of skin under vacuum. When blood is brought closer to the surface of the skin, light capable of lower penetration depth can be used, thereby reducing the unwanted signals of light absorption or light scattering attributable to the tissue that does not comprise blood.

Figure 5C:
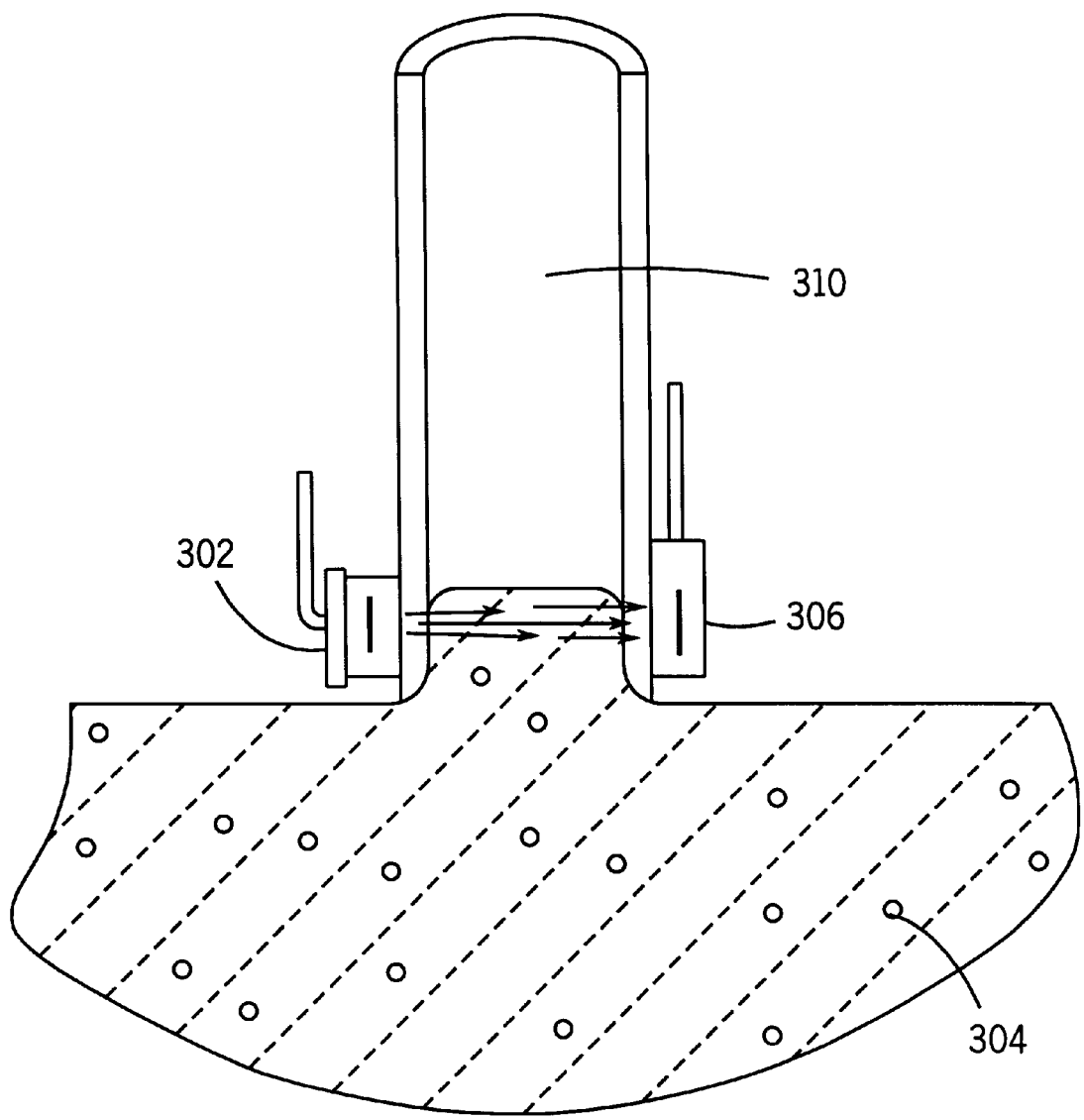

FIGS. 5A, 5B, and 5C illustrate a photometer unit 300 that has the capability of increasing the local supply of blood to a body part. This photometer unit is small enough to be held in the hand of a person. The photometer unit 300 includes a plurality of light sources 302 of selected wavelengths. The light sources are either laser diodes or light emitting diodes. The light sources emit light of discrete wavelengths sequentially to impinge on a body part 304. The rate of the emitting sequence should be sufficiently high (e.g., greater than 500 Hz) to achieve the concurrency requirement, i.e., observing with substantially the same optical arrangement at substantially the same time on substantially the same position on the body part. The light reaches the detector 306 at the side of the body part opposite to that of the light source. A vacuum pump 308 generates and maintains a low vacuum on the body part to draw blood-engorged skin and tissue into an observation area defined by hollow tubing 310. A lever 312 driven by motor 314 is used to adjust the distance between the light source and the detector, i.e. path-length, for optimal reading on the detector. The power source 316, the controlling electronic 318, and the processor units 320 are shown as an example of one of the many possible ways of implementing the electronics. The results after the data is processed are shown in the display 322 for blood glucose concentration. The switch 324 is used for switching the instrument on and off. The optical arrangement can be of the type illustrated in FIG. 1 and FIG. 2.

A calibration scheme can be developed through multivariate analysis to correlate the in vivo optical measurement with the concentration of the analyte of interest in tissue. Methods of multivariate analysis are well known to those skilled in the art. These methods include classical least squares, partial least squares, principle component analysis, and neural networks. With the mathematical coefficients determined as parameters through calibration, the optical measurements of improved precision can be converted to concentration of the analyte of interest by standard mathematical operations. Known concentrations of the analyte of interest can be obtained by previously conducted in vivo or in vitro tests. The results of the previously conducted tests can be programmed into a data processor and used to predict concentrations of analytes by means of algorithms derived empirically.

The following non-limiting examples are provided to further illustrate the invention.

EXAMPLES

Example 1

This example demonstrates how calculating the ratio of the output signals of two channels can be used to improve consistency in non-invasive optical measurements. An instrument as shown in FIG. 1 was used for this example. High-speed electronics were used to allow recording through a finger at a rate of one data point per 2 ms, 2048 data points per recording. A protocol was used to demonstrate the reduction of variation by taking multiple readings of a finger in the instrument without removing the finger, as well as variations with multiple re-insertions of the finger into the instrument. In this protocol, the procedure of recording involved taking five recordings with one finger insertion, the finger staying motionless in the instrument during the five recordings. The finger was then withdrawn from the instrument after this series of five recordings. This series of inserting a finger, taking five recordings, and withdrawing the finger is called a "run". The run is repeated five times in this protocol. The variation within the five recordings in each run, "within run variation", would be estimating the variation of readings with the finger remaining motionless during recording. The variation among the average value of each run, "between run variation", would be estimating the variation resulting from finger insertion.

Figure 3:
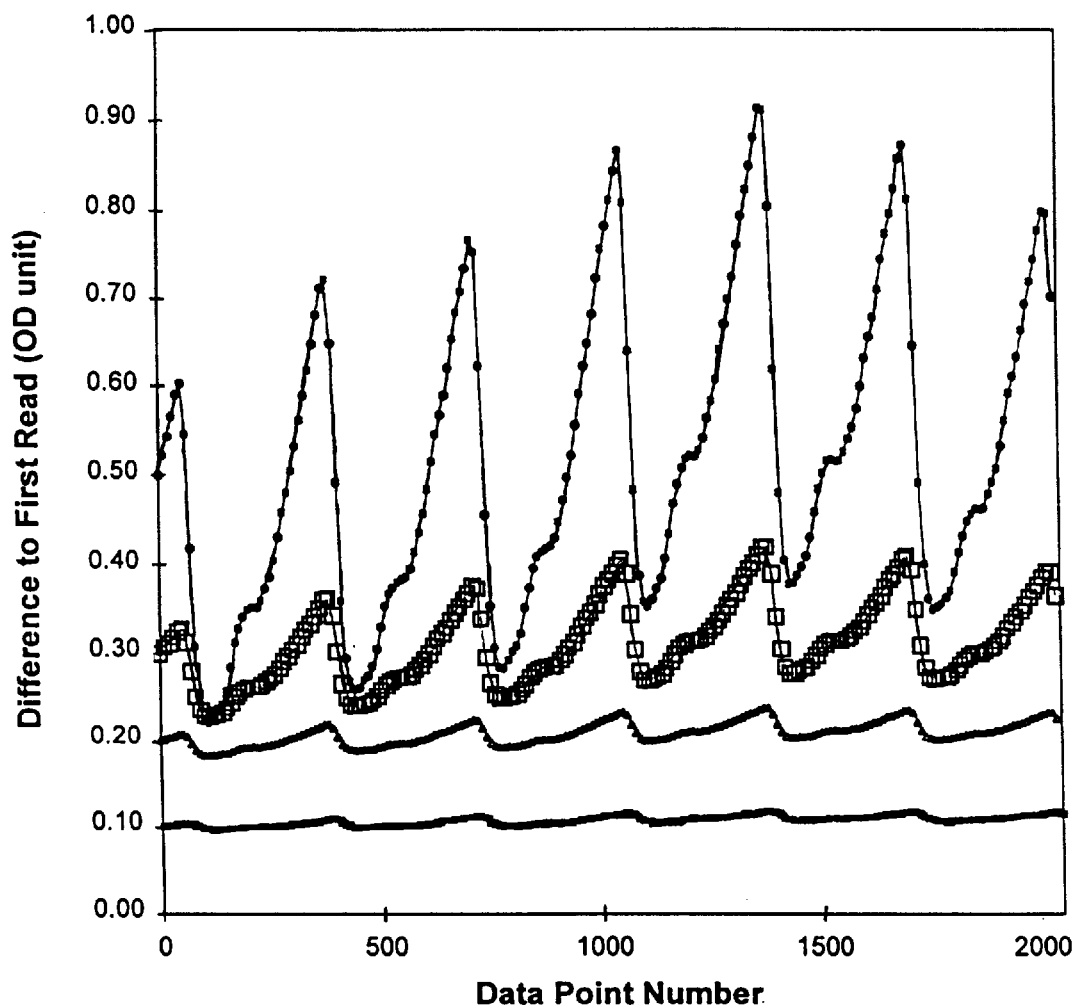
FIG. 3 is a graph illustrating data obtained by means of a device equivalent to the one shown in FIG. 1. The raw data were processed by calculating the difference between a given reading and the first reading within each channel and plotting the difference calculated against the corresponding data point. Because data were collected at fixed intervals, each data point number is equivalent to an interval of time elapsed during the period of data collection. For the purpose of clarity, the plot of each channel was given an offset value so that it would not obscure that of another channel. Offsets of 0.5, 0.3, 0.2, and 0.1 were added to channel A (—♦—), channel B (—●—), channel C (—Δ—), and channel D (———), respectively.
Figure 4:
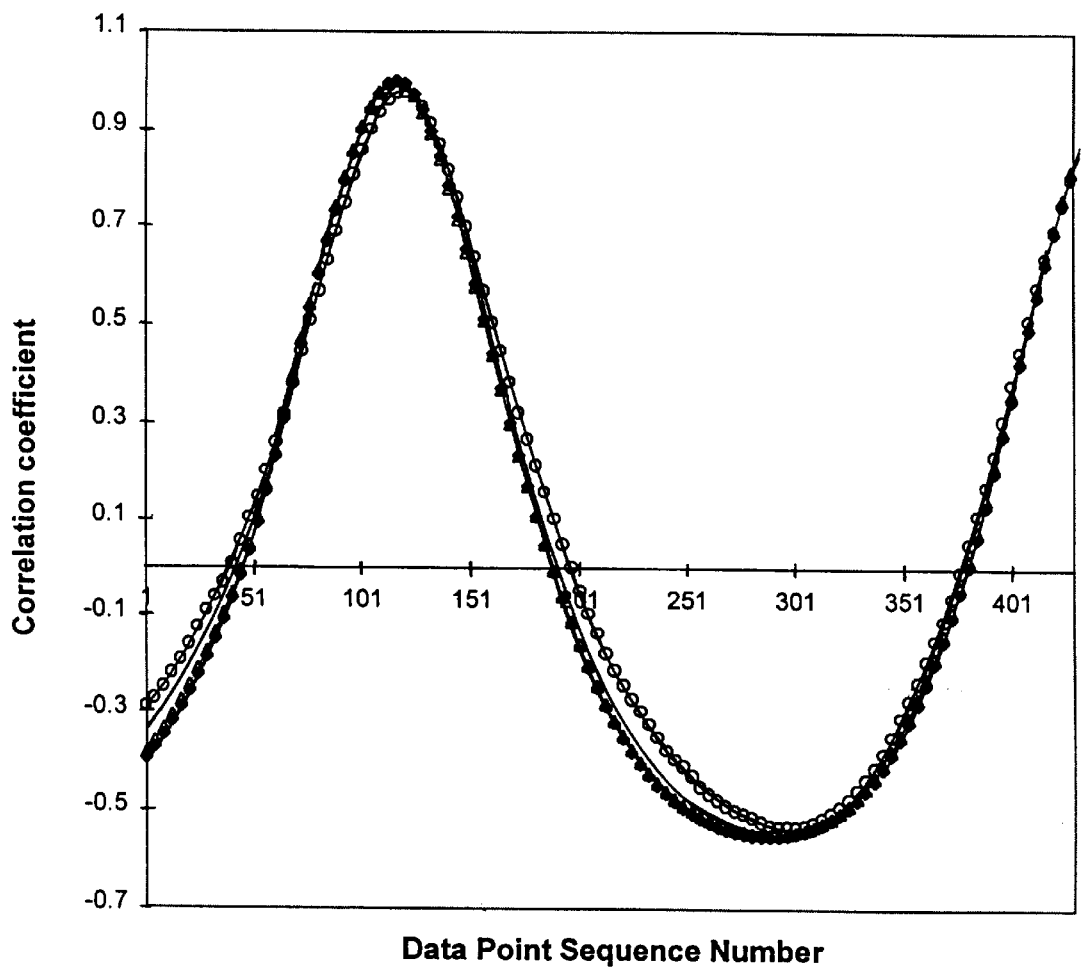
FIG. 4 is a graph illustrating the correlation function with each of the three measurement channels (—♦—, —●—, —Δ—), and one reference channel (—). The time delay between each channel was 2 milliseconds. A segment of data comprising about 300 data points was selected as correlation reference. This reference data segment started from the first minimum and ended at the second minimum in channel A of FIG. 3.

FIG. 3 shows curves of the data of four channels, as an example, in one recording of this protocol. The data in these curves have been processed to enhance clarity. To avoid the offset difference from channel to channel, the value of the first data point in a given channel is subtracted from the values of the remaining data points of that channel. To avoid showing data in curves overlying one another, different offset values were added to the values in the different channels to separate the curves. This step is carried out for display purposes only and is not included in the typical data collection scheme described below. The pulse through the finger, which reflects heartbeats, is clearly observable in these curves. The heartbeats were similar but not identical. Because data collection in this example was not synchronous with the heartbeat from run to run, each run of data would have a different number of complete pulses. To ensure comparing consistent experimental observations both within a run and between runs, only the portion of data for an integral number of heartbeats was used for further processing.

The first technique for processing these data involved identifying the peak (high value) and valley (low value) of the recording for each complete pulse segment and then averaging all the measured values between the limit of these two points. This averaged value is a number representing the mean value of a pulse segment for the measurement. Because there are five complete pulses in the measurement shown in FIG. 3, the mean values of these five pulses were further averaged to yield a number herein designated as "Pulse Averaged Value." This Pulse Averaged Value for a given channel for a given run is shown in Table 4. The statistical analysis of the 25 such Pulse Averaged Values is shown in Table 5. All four channels showed lower standard deviation for within run statistics (effect of one finger insertion for each of the five runs) than that for between run statistics (effect of five finger insertions in the 25 runs). These results are consistent with conventional state-of-the arts studies. These results indicate that a major contribution to total variation was attributable to reinsertion of the finger into the instrument. The success of this invention can be seen when these variations can be reduced significantly by using the device and method of this invention. Within the course of the study, the lamp was sufficiently stable that the total CV of the lamp was about 0.02%, and therefore contributed little to the variation of in vivo measurements.

The advantage of the invention is apparent upon analysis of the results of the ratios of the signals of measurement channels to that of a reference channel. Table 6 shows the calculated value of the ratio of the signal of each channel to that of channel B, which was chosen as reference channel. For the purpose of ease in comparing the results to Table 4, each ratio is scaled to an equivalent magnitude by multiplying by 100,000. The entry in each cell of Table 6 is obtained by dividing the value in each channel in a given row in Table 4 by the value of channel B in that row of Table 4 and then multiplying that ratio by 100,000. Table 7 shows statistics for comparing "within run" and "between run" variations, in the manner described for Table 5. Improvement in total CV for all measuring channels is apparent when comparing the last row in Table 5 and Table 7. The CVs decreased from 4.9% to 0.6% for channel A, 3.3% to 1.7% for channel C, and 4.1% to 1.7% for channel D. These data show that the improvement is a 2 to 8 fold decrease of total CV. This improvement is significant and it shows that better results for determinations of concentrations of analytes are obtainable.

TABLE 4

Pulse Averaged Value of the Optical Readings through a Finger

| Observation | Finger insertion | Recording channel A | B | C | D | Lamp |
|---|---|---|---|---|---|---|
| 1 | 1 | 249332.0 | 297674.5 | 179992.9 | 63968.4 | 99788.7 |
| 2 | 1 | 254884.5 | 304380.4 | 184059.0 | 66280.7 | 99806.4 |
| 3 | 1 | 253015.0 | 302852.2 | 184231.8 | 66378.7 | 99786.7 |
| 4 | 1 | 251775.6 | 301806.9 | 184365.3 | 66464.8 | 99774.8 |
| 5 | 1 | 256746.9 | 307128.8 | 186115.0 | 67137.7 | 99739.3 |
| 6 | 2 | 243203.1 | 291577.4 | 178469.7 | 64418.9 | 99738.7 |
| 7 | 2 | 258072.2 | 307704.1 | 184807.2 | 66877.3 | 99743.4 |
| 8 | 2 | 259386.5 | 309326.0 | 185843.0 | 67143.1 | 99735.2 |
| 9 | 2 | 250008.5 | 300153.1 | 184048.9 | 66802.5 | 99740.0 |
| 10 | 2 | 258274.6 | 308784.6 | 186755.5 | 67676.0 | 99762.1 |
| 11 | 3 | 211443.6 | 257860.0 | 164925.6 | 58446.0 | 99778.2 |
| 12 | 3 | 232463.6 | 280862.1 | 173806.4 | 62056.2 | 99772.3 |
| 13 | 3 | 238666.1 | 287844.5 | 176992.2 | 63379.7 | 99775.0 |
| 14 | 3 | 238204.6 | 287763.0 | 177622.8 | 63756.4 | 99774.4 |
| 15 | 3 | 237188.0 | 287047.2 | 177996.5 | 63978.9 | 99791.6 |
| 16 | 4 | 254804.8 | 304355.9 | 183746.7 | 66995.0 | 99791.4 |
| 17 | 4 | 255761.3 | 305898.7 | 185436.6 | 67657.8 | 99779.0 |
| 18 | 4 | 256038.8 | 306509.7 | 186256.1 | 67957.7 | 99779.4 |
| 19 | 4 | 256477.3 | 307067.4 | 186652.0 | 67869.1 | 99739.3 |
| 20 | 4 | 254511.2 | 305374.8 | 186610.0 | 68009.9 | 99747.4 |
| 21 | 5 | 245816.3 | 295877.5 | 182217.7 | 66475.6 | 99746.1 |
| 22 | 5 | 263369.1 | 314706.8 | 189139.2 | 68992.0 | 99794.5 |
| 23 | 5 | 252842.5 | 304128.3 | 187037.9 | 68296.9 | 99773.4 |
| 24 | 5 | 255437.8 | 307065.6 | 188436.6 | 68853.4 | 99787.8 |
| 25 | 5 | 241834.6 | 293398.3 | 185406.8 | 67994.0 | 99782.4 |

TABLE 5

Statistical Analysis of the Results in Table 4

| Finger insert number | Statistic | Recording channel A | B | C | D | Lamp |
|---|---|---|---|---|---|---|
| 1 | Average | 253150.8 | 302768.6 | 183752.8 | 66046.1 | 99779.2 |
|   | Std. Dev. | 2847.4 | 3481.8 | 2259.2 | 1209.3 | 25.0 |
|   | CV (%) | 1.12 | 1.15 | 1.23 | 1.83 | 0.03 |
| 2 | Average | 253789.0 | 303509.0 | 183984.9 | 66583.6 | 99743.9 |
|   | Std. Dev. | 7002.7 | 7630.4 | 3249.1 | 1257.6 | 10.6 |
|   | CV (%) | 2.76 | 2.51 | 1.77 | 1.89 | 0.01 |
| 3 | Average | 231593.2 | 280275.4 | 174268.7 | 62323.4 | 99778.3 |
|   | Std. Dev. | 11530.4 | 12864.7 | 5478.8 | 2292.1 | 7.7 |
|   | CV (%) | 4.98 | 4.59 | 3.14 | 3.68 | 0.01 |
| 4 | Average | 255518.7 | 305841.3 | 185740.3 | 67697.9 | 99767.3 |
|   | Std. Dev. | 832.6 | 1046.1 | 1216.6 | 415.3 | 22.6 |
|   | CV (%) | 0.33 | 0.34 | 0.65 | 0.61 | 0.02 |
| 5 | Average | 251860.1 | 303035.3 | 186447.6 | 68122.4 | 99776.8 |
|   | Std. Dev. | 8415.2 | 8628.0 | 2762.5 | 1006.2 | 18.8 |
|   | CV (%) | 3.34 | 2.85 | 1.48 | 1.48 | 0.02 |
| Pooled Within run | Average | 249182.3 | 299085.9 | 182838.9 | 66154.7 | 99769.1 |
|   | Std. Dev. | 7233.3 | 7891.6 | 3310.3 | 1377.1 | 18.2 |
|   | CV (%) | 2.90 | 2.64 | 1.81 | 2.08 | 0.02 |
| Between run | Std. Dev. | 9378.3 | 9979.7 | 4697.6 | 2214.2 | 12.4 |
|   | CV (%) | 3.76 | 3.34 | 2.57 | 3.35 | 0.01 |
| Total Statistics | Std. Dev. | 12277.5 | 13203.2 | 5934.4 | 2679.3 | 23.5 |
|   | CV (%) | 4.9 | 4.4 | 3.3 | 4.1 | 0.02 |

TABLE 6

Pulse Averaged Value after Calculating the Ratio of Measurement in Each Channel to That in Channel B and then Scaled to a Magnitude Suitable for Comparison to Table 4

| Observation | Finger insertion | Scaled ratio value of each channel | | | |
|---|---|---|---|---|---|
| | | A | B | C | D |
| 1 | 1 | 83759.9 | 100000.0 | 60466.3 | 21489.4 |
| 2 | 1 | 83738.8 | 100000.0 | 60470.1 | 21775.6 |
| 3 | 1 | 83544.1 | 100000.0 | 60832.2 | 21917.9 |
| 4 | 1 | 83422.7 | 100000.0 | 61087.2 | 22022.3 |
| 5 | 1 | 83595.8 | 100000.0 | 60598.4 | 21859.8 |
| 6 | 2 | 83409.4 | 100000.0 | 61208.3 | 22093.2 |
| 7 | 2 | 83870.3 | 100000.0 | 60060.0 | 21734.3 |
| 8 | 2 | 83855.4 | 100000.0 | 60080.0 | 21706.3 |
| 9 | 2 | 83293.7 | 100000.0 | 61318.3 | 22256.1 |
| 10 | 2 | 83642.3 | 100000.0 | 60480.8 | 21916.9 |
| 11 | 3 | 81999.4 | 100000.0 | 63959.4 | 22665.8 |
| 12 | 3 | 82767.9 | 100000.0 | 61883.2 | 22094.9 |
| 13 | 3 | 82914.9 | 100000.0 | 61488.8 | 22018.7 |
| 14 | 3 | 82778.0 | 100000.0 | 61725.4 | 22155.9 |
| 15 | 3 | 82630.3 | 100000.0 | 62009.5 | 22288.6 |
| 16 | 4 | 83719.4 | 100000.0 | 60372.3 | 22012.1 |
| 17 | 4 | 83609.8 | 100000.0 | 60620.3 | 22117.7 |
| 18 | 4 | 83533.7 | 100000.0 | 60766.8 | 22171.5 |
| 19 | 4 | 83524.8 | 100000.0 | 60785.4 | 22102.3 |
| 20 | 4 | 83343.9 | 100000.0 | 61108.5 | 22271.0 |
| 21 | 5 | 83080.4 | 100000.0 | 61585.5 | 22467.3 |
| 22 | 5 | 83687.1 | 100000.0 | 60100.1 | 21922.6 |
| 23 | 5 | 83136.8 | 100000.0 | 61499.7 | 22456.6 |
| 24 | 5 | 83186.7 | 100000.0 | 61366.9 | 22423.0 |
| 25 | 5 | 82425.4 | 100000.0 | 63192.9 | 23174.6 |

TABLE 7

Statistical Analysis of the Results in Table 6

| Finger insert number | Statistic | Recording channel | | | |
|---|---|---|---|---|---|
| | | A | B | C | D |
| 1 | Average | 83612.3 | 100000.0 | 60690.8 | 21813.0 |
| | Std. Dev. | 140.2 | 0.0 | 266.8 | 201.9 |
| | CV (%) | 0.17 | 0.00 | 0.44 | 0.93 |
| 2 | Average | 83614.2 | 100000.0 | 60629.5 | 21941.4 |
| | Std. Dev. | 259.4 | 0.0 | 603.7 | 235.0 |
| | CV (%) | 0.31 | 0.00 | 1.00 | 1.07 |
| 3 | Average | 82618.1 | 100000.0 | 62213.2 | 22244.8 |
| | Std. Dev. | 360.2 | 0.0 | 995.3 | 255.3 |
| | CV (%) | 0.44 | 0.00 | 1.60 | 1.15 |
| 4 | Average | 83546.3 | 100000.0 | 60730.6 | 22134.9 |
| | Std. Dev. | 137.5 | 0.0 | 268.2 | 95.3 |
| | CV (%) | 0.16 | 0.00 | 0.44 | 0.43 |
| 5 | Average | 83103.3 | 100000.0 | 61549.0 | 22488.8 |
| | Std. Dev. | 449.7 | 0.0 | 1099.8 | 446.3 |
| | CV (%) | 0.54 | 0.00 | 1.79 | 1.98 |
| Pooled Within run | Average | 83298.8 | 100000.0 | 61162.7 | 22124.6 |
| | Std. Dev. | 295.9 | 0.0 | 735.9 | 271.8 |
| | CV (%) | 0.36 | 0.00 | 1.20 | 1.23 |
| Between run | Std. Dev. | 415.5 | 0.0 | 615.1 | 233.9 |
| | CV (%) | 0.50 | 0.00 | 1.01 | 1.06 |
| Total Statistics | Std. Dev. | 527.0 | 0.0 | 1014.0 | 378.6 |
| | CV (%) | 0.63 | 0.00 | 1.66 | 1.71 |

Example 2

One of the recognized variables in an in vivo measurement is the fluctuation of blood volume at the measurement site. Fluctuation of blood volume at the measurement site could result from such factors as lack of anatomical homogeneity, blood vessel dilation or constriction due to hormonal control, or change in ambient temperature. Because the volume fraction of blood in a body part is not constant, there could be confusion in interpreting a result that indicates that an in vivo signal has been doubled. One extreme of the possibilities is that the concentration of an analyte, such as glucose, has increased two-fold while volume of blood in the finger has remained unchanged. Another extreme is that the concentration of that analyte has remained unchanged while the volume of blood inside finger has increased two-fold. There are too many possible ways to combine different variations of these parameters to allow a simple interpretation of the observed result. One of the ways to address this problem is to apply the technique of calculating ratios of a special parameter, as described in this invention.

The basic principle of this technique involves the understanding of blood flow that is generated by cardiac output. Cardiac output is an expression describing the amount of blood that has been pumped by the heart to push it through the circulation system per unit of time. For example, a heartbeat rate of 60 pulses per minute with a flow rate of 5 mL per pulse will have a cardiac output of 300 mL per minute. The amount of blood flow in the site being observed, such as a finger, is similarly defined as the pulse rate multiplied by the amount of blood transported per pulse. The amount of blood flow is difficult to measure. The pulse rate and the differences of optical parameters are readily measurable. When more blood appears in the finger immediately after a heart contraction, the measured light intensity is decreased because the greater amount of blood absorbs a greater amount of light. When the heart relaxes to take in more blood in preparation for the next contraction, less blood appears in the finger and the measured light intensity is increased because the lesser amount of blood absorbs a lesser amount of light. The difference of the measurement from the systolic phase (contracting) to the diastolic phase (relaxing) is therefore proportional to the amount of blood pumped per pulse. The total number of data measurements from the peak of one pulse to the peak of the next pulse are recorded during the duration of one pulse under the condition that the data are collected at constant intervals. The shorter the duration of one pulse, the more pulses occur in a given period of time. The product of the difference of peak measurement to valley measurement multiplied by the number of pulses per unit time would therefore generate an estimate of blood flow. Replacing the number of a given pulse with the reciprocal of the duration of each pulse, the estimate of blood flow is equivalent to dividing the peak to valley measurement difference by the number of data points. Therefore, the quotient obtained by dividing the amplitude difference by the number of data points, i.e., a mathematical operation of calculating slope, would yield a number proportional to blood flow. A greater pulse amplitude will exhibit a higher observed slope if the pulse rate remains constant. Similarly, a higher pulse rate will exhibit a higher observed slope if the pulse amplitude remains constant. Thus, it is clear that the slope of the observed signal is proportional to blood flow. Even though the slope of the observed signal is as variable as that of the blood flow, this finding is important because all of the channels have been observing the same blood flow concurrently. This common blood flow can be utilized by applying the ratio calculation method of this invention.

An example given below demonstrates the improvement in data reproducibility. This example uses the same data that was used in Example 1. Instead of the Pulse Averaged Value as shown in Table 4, the processing of the slope for each pulse is used in this example. The slope value of each pulse was calculated from a straight line fitted to the innermost 60% of the data points from the peak value of a pulse to the valley value of that pulse. This method of slope calculation is more precise than that of simply dividing the difference of peak value and valley value by the number of data points from peak to valley. This method is less sensitive to errors that arise in picking the peak value and the valley value of each pulse. By calculating the average of the values of the slopes from the five pulses in FIG. 3, a value designated as the "Pulse Averaged Slope" is derived. The listing of the Pulse Averaged Slope for all 25 runs is shown in Table 8. The statistical analysis of the Pulse Averaged Slopes is shown in Table 9. Up to this point, the data processing methods are conventional state-of-the-art methods lacking the benefit of this invention. It is therefore not surprising to find high variability of the results, which is evident from the high values of the CV for both the "within run" comparison (with the same finger insertion) and the "between run" comparison (with finger reinsertion).

The results of normalizing the measurement channel data by the reference channel data are discussed below. Table 10 shows the calculated Pulse Averaged Slope after normalizing to channel B as the reference channel. The statistical analysis of the results in Table 10 is shown in Table 11. From comparing the last row of Table 9 to the last row of Table 11, it is apparent that there is significant improvement of CV for all measuring channels. CV decreased from 23.2% to 0.6% through the use of this invention for channel A. Similarly, CV decreased from 23.6% to 1.3% for channel C, and 21.9% to 4.1% for channel D. These data show that the improvement (decrease) in CV ranges from 5-fold to 40-fold. The CV improvement has practical implications as to whether a robust mathematical scheme could be developed for practical use. It is apparent that high variation as suggested by a high value of CV would not be consistent enough to allow robust calibration. It would be extremely difficult to have good performance by applying a calibration model to the unknown new data when the data of calibration have more than 20% CV. A benchmark value is about 5% CV for supporting a practical calibration in chemical assay or immunoassay currently on the market place. As shown in this example, reducing the high variability in the in vivo data by the invention improved CV by an average of 20-fold. With the variation reduced to less than 5% CV, it is reasonable that a robust calibration scheme could be built for the in vivo measurement, similar to the results of the more conventional chemical assay or immunoassay.

TABLE 8

Pulse Averaged Slope Value of the Optical Readings through a Finger

| Reading no. | Finger insertion number | Pulse averaged slope in recording channel | | | |
|---|---|---|---|---|---|
| | | A | B | C | D |
| 1 | 1 | 2241.5 | 1902.1 | 787.6 | 632.3 |
| 2 | 1 | 2185.6 | 1849.8 | 768.1 | 595.7 |
| 3 | 1 | 2240.0 | 1895.8 | 784.2 | 592.3 |
| 4 | 1 | 2184.5 | 1850.0 | 770.4 | 619.5 |
| 5 | 1 | 2228.2 | 1886.5 | 784.9 | 663.8 |
| 6 | 2 | 1896.1 | 1608.9 | 658.8 | 501.3 |
| 7 | 2 | 1528.0 | 1291.8 | 537.4 | 431.0 |
| 8 | 2 | 2116.3 | 1788.7 | 738.2 | 593.6 |
| 9 | 2 | 2051.2 | 1737.9 | 716.5 | 547.0 |
| 10 | 2 | 2041.7 | 1730.9 | 720.8 | 572.8 |
| 11 | 3 | 2560.4 | 2202.3 | 937.7 | 736.4 |
| 12 | 3 | 2629.6 | 2246.1 | 936.4 | 722.1 |
| 13 | 3 | 2659.5 | 2271.7 | 954.8 | 744.8 |
| 14 | 3 | 2645.4 | 2258.7 | 945.9 | 731.5 |
| 15 | 3 | 2843.8 | 2427.9 | 1015.7 | 823.6 |
| 16 | 4 | 1791.7 | 1527.3 | 648.7 | 514.5 |
| 17 | 4 | 2227.7 | 1894.1 | 794.3 | 620.9 |
| 18 | 4 | 2436.6 | 2074.5 | 867.3 | 664.1 |
| 19 | 4 | 2804.1 | 2394.2 | 1009.6 | 754.4 |
| 20 | 4 | 2814.7 | 2403.7 | 1016.5 | 790.3 |
| 21 | 5 | 2457.8 | 2105.9 | 882.6 | 686.6 |
| 22 | 5 | 2074.6 | 1779.2 | 769.0 | 638.9 |
| 23 | 5 | 2949.4 | 2525.6 | 1055.4 | 819.5 |
| 24 | 5 | 3123.3 | 2680.5 | 1125.0 | 884.0 |
| 25 | 5 | 4068.7 | 3500.5 | 1442.5 | 1062.0 |

TABLE 9

Statistical Analysis of the Results in Table 8

| Finger insertion number | Statistic | Recording channel | | | |
|---|---|---|---|---|---|
| | | A | B | C | D |
| 1 | Average | 2216.0 | 1876.8 | 779.0 | 620.7 |
| | Std. Dev. | 28.7 | 25.2 | 9.1 | 29.3 |
| | CV (%) | 1.29 | 1.34 | 1.16 | 4.71 |
| 2 | Average | 1926.7 | 1631.6 | 674.3 | 529.1 |
| | Std. Dev. | 236.9 | 201.1 | 82.2 | 64.8 |
| | CV (%) | 12.30 | 12.33 | 12.19 | 12.24 |
| 3 | Average | 2667.7 | 2281.3 | 958.1 | 751.7 |
| | Std. Dev. | 105.5 | 86.0 | 33.0 | 41.0 |
| | CV (%) | 3.96 | 3.77 | 3.45 | 5.46 |
| 4 | Average | 2415.0 | 2058.8 | 867.3 | 668.8 |
| | Std. Dev. | 428.7 | 367.9 | 154.6 | 109.8 |
| | CV (%) | 17.75 | 17.87 | 17.83 | 16.41 |
| 5 | Average | 2934.8 | 2518.3 | 1054.9 | 818.2 |
| | Std. Dev. | 756.5 | 653.3 | 258.2 | 168.3 |
| | CV (%) | 25.78 | 25.94 | 24.47 | 20.56 |
| Pooled Within run | Average | 2432.0 | 2073.4 | 866.7 | 677.7 |
| | Std. Dev. | 406.0 | 349.5 | 140.3 | 97.1 |
| | CV (%) | 16.69 | 16.86 | 16.19 | 14.32 |
| Between run | Std. Dev. | 346.0 | 307.2 | 134.8 | 103.8 |
| | CV (%) | 14.23 | 14.82 | 15.55 | 15.31 |
| Total statistics | Std. Dev. | 563.5 | 490.9 | 204.5 | 148.6 |
| | CV (%) | 23.17 | 23.67 | 23.59 | 21.92 |

TABLE 10

Pulse Averaged Value after Calculating the Ratio of
Measurement in Each Channel to That in Channel B and
then Scaled to a Magnitude Suitable for Comparison to Table 8

| Reading number | Finger insertion number | Scaled Normalized Value of Pulse Averaged Slope | | | |
|---|---|---|---|---|---|
| | | A | B | C | D |
| 1 | 1 | 117843.4 | 100000.0 | 41406.9 | 33242.2 |
| 2 | 1 | 118153.3 | 100000.0 | 41523.4 | 32203.5 |
| 3 | 1 | 118155.9 | 100000.0 | 41365.1 | 31242.7 |
| 4 | 1 | 118081.1 | 100000.0 | 41643.2 | 33486.5 |
| 5 | 1 | 118112.9 | 100000.0 | 41606.1 | 35186.9 |
| 6 | 2 | 117850.7 | 100000.0 | 40947.2 | 31157.9 |
| 7 | 2 | 118284.6 | 100000.0 | 41600.9 | 33364.3 |
| 8 | 2 | 118315.0 | 100000.0 | 41270.2 | 33186.1 |
| 9 | 2 | 118027.5 | 100000.0 | 41227.9 | 31474.8 |
| 10 | 2 | 117956.0 | 100000.0 | 41643.1 | 33092.6 |
| 11 | 3 | 116260.3 | 100000.0 | 42578.2 | 33437.8 |
| 12 | 3 | 117074.0 | 100000.0 | 41690.0 | 32149.1 |
| 13 | 3 | 117070.9 | 100000.0 | 42030.2 | 32786.0 |
| 14 | 3 | 117120.5 | 100000.0 | 41878.1 | 32385.9 |
| 15 | 3 | 117130.0 | 100000.0 | 41834.5 | 33922.3 |
| 16 | 4 | 117311.6 | 100000.0 | 42473.6 | 33686.9 |
| 17 | 4 | 117612.6 | 100000.0 | 41935.5 | 32780.7 |
| 18 | 4 | 117454.8 | 100000.0 | 41807.7 | 32012.5 |
| 19 | 4 | 117120.5 | 100000.0 | 42168.6 | 31509.5 |
| 20 | 4 | 117098.6 | 100000.0 | 42289.0 | 32878.5 |
| 21 | 5 | 116710.2 | 100000.0 | 41910.8 | 32603.6 |
| 22 | 5 | 116603.0 | 100000.0 | 43221.7 | 35909.4 |
| 23 | 5 | 116780.2 | 100000.0 | 41788.1 | 32447.7 |
| 24 | 5 | 116519.3 | 100000.0 | 41969.8 | 32978.9 |
| 25 | 5 | 116232.0 | 100000.0 | 41208.4 | 30338.5 |

TABLE 11

Statistical Analysis of the Results in Table 10

| Finger insertion number | Statistic | Recording channel | | | |
|---|---|---|---|---|---|
| | | A | B | C | D |
| 1 | Average | 118069.3 | 100000.0 | 41509.0 | 33072.4 |
| | Std. Dev. | 130.0 | 0.0 | 121.2 | 1481.0 |
| | CV (%) | 0.11 | 0.00 | 0.29 | 4.48 |
| 2 | Average | 118086.7 | 100000.0 | 41337.9 | 32455.1 |
| | Std. Dev. | 204.7 | 0.0 | 287.9 | 1050.1 |
| | CV (%) | 0.17 | 0.00 | 0.70 | 3.24 |
| 3 | Average | 116931.1 | 100000.0 | 42002.2 | 32936.2 |
| | Std. Dev. | 376.0 | 0.0 | 344.1 | 736.4 |
| | CV (%) | 0.32 | 0.00 | 0.82 | 2.24 |
| 4 | Average | 117319.6 | 100000.0 | 42134.9 | 32573.6 |
| | Std. Dev. | 219.5 | 0.0 | 267.6 | 840.0 |
| | CV (%) | 0.19 | 0.00 | 0.64 | 2.58 |
| 5 | Average | 116568.9 | 100000.0 | 42019.8 | 32855.6 |
| | Std. Dev. | 213.2 | 0.0 | 736.7 | 1994.1 |
| | CV (%) | 0.18 | 0.00 | 1.75 | 6.07 |
| Pooled Within run | Average | 117395.2 | 100000.0 | 41800.7 | 32778.6 |
| | Std. Dev. | 242.4 | 0.0 | 407.5 | 1305.4 |
| | CV (%) | 0.21 | 0.00 | 0.97 | 3.98 |
| Between run | Std. Dev. | 668.9 | 0.0 | 0.0 | 0.0 |
| | CV (%) | 0.57 | 0.00 | 0.00 | 0.00 |
| Total Statistics | Std. Dev. | 719.6 | 0.0 | 539.4 | 1330.4 |
| | CV (%) | 0.61 | 0.00 | 1.29 | 4.06 |

Example 3

One of the recognized variables in in vivo measurements is the fluctuation of blood volume at the measurement site. Fluctuation of blood volume at the measurement site could be caused by one or more factors in varying degrees. Example 2 discussed variation in blood flow resulting from the heartbeat and changes of blood vessel diameter under parasympathetic nerve and endocrine control. Other factors such as oxygen saturation variation due to breathing, changes in blood constituents due to a meal, changes in hydration, and changes in posture could cause blood volume to fluctuate. In a manner similar to the variation caused by heartbeat, the elevation of the heart relative to the finger should have an effect through changes of hydrostatic head. When a person changes from a sitting position to a standing position without moving the finger, an additional hydrostatic head of pressure should result on account of the difference in height of the heart. This pressure should result in providing more blood in the finger. This pressure could also increase or reduce the amplitude of the pulse, depending on the elasticity of the blood vessels in an individual's finger. If the blood vessels are very elastic (such as in a young person or in a person with little fatty deposit on the vessel wall), the additional pressure might increase the amplitude of the pulse as the vessels contract or expand. If the blood vessels are not very elastic (due to old age or fatty deposits on the vessel wall), the additional pressure might reduce the amplitude of the pulse because of the rigidity of the walls of the vessels. Recognizing this variability for control or compensating for its effect is essential for success in determining the concentration of an analyte in blood in vivo non-invasively.

An instrument as in Example 1 was used for this example. Three channels of the instrument were used to allow recording at a rate of one data point per 2 ms, 8192 data points per recording, through a finger. A protocol was used to make recording first in the sitting position and then in the standing position. The procedure for recording the data was repeated three times without removing the finger from the instrument. Both data analysis methods that were described above in Example 1 and Example 2 were used in this example.

Table 12 shows the results from processing the data. Both the method of calculating the Pulse Averaged Value (as used in Table 4 for Example 1) and the Pulse Averaged Slope (as used in Table 8 for Example 2) are used in this example. The Pulse Averaged Values are shown in the left-hand side of the table while the Pulse Averaged Slopes are shown in the right-hand side of the table. Table 13 provides the statistical analysis of Table 12, comparing results from the sitting position and results from the standing position. The higher average values in each of the three channels in the repetitions for the sitting position as compared with the corresponding values in the repetitions for the standing position indicate that more light passed through the finger to reach the detector when the subject was in the sitting position. In other words, a finger is more transparent to light when the subject was in the sitting position. The Pulse Averaged Slope for all three channels when the subject was in the sitting position were lower than the corresponding values for all three channels when the subject was in the standing position, thereby indicating that the pulse was amplified by standing. Variation, expressed in CV %, was slightly lower for the Pulse Averaged Value results when the subject was in the sitting position than when the subject was in the standing position. Variation was slightly lower for the Pulse Averaged Slope results when the subject was in the standing position than when the subject was in the sitting position. However, the variation in each of the channels, either in Pulse Averaged Value (CV=5% to 7% CV) or in Pulse Average Slope value (CV=18% to 26%), was too high to ensure adequate precision for in vivo measurement of the concentration of an analyte.

The improvement resulting from the method of this invention, i.e., to normalize away the common variations, is discussed below. Table 14 shows the result of normalizing the values in Table 12 (the Pulse Averaged Value in the left-hand-side of table and the Pulse Averaged Slope in the right-hand-side) using channel B as the reference channel. The results of statistical analysis of the data in Table 14 are shown in Table 15. The improvement of measurement reproducibility shown by the reduction of CV is apparent, from 5% to 7% reduced to 0.4 to 1.5% for the Pulse Averaged Values, and from 18% to 26% reduced to 0.4% to 5% for the Pulse Averaged Slope. The difference between results obtained from measurements in the sitting position versus the results obtained from measurements in the standing position was also reduced. The difference of average values (172401.3−137222.2=35179.1, or 20% of the sitting position value as shown in column 3 of Table 13) is rather high. After calculating the ratio of the measurement in channel A to that in channel B, the magnitude of this difference in channel A is significantly reduced (85942.0−83841.7=2100.3, or 2% of the sitting position value, as shown in column 3 of Table 15). These results support the interpretation that the difference in the sitting position measurements versus the standing position measurements is related to the difference in the blood volume fraction in the finger. In the short duration of this experiment, with the subject in a fasting state, the glucose concentration within the blood stream is relatively stable and is unlikely to be related to the observed difference in optical readings.

It is apparent to anyone skilled in the art that a more reproducible result would always be more likely obtainable with a more consistent experimental protocol. Thus postures as drastically different as sitting versus standing should not be mixed in a normal protocol. The purpose of this example was not to advocate relaxing the practice of a normal protocol. Instead, the purpose was to show that this invention has the capability to reduce variation, which in turn would be very helpful for removing the adverse effects of factors that are not as controllable as posture by experimental protocol alone. For example, significant improvement in the in vivo measurements can be made through the use of this invention to reduce variation due to heartbeat, oxygen saturation variation due to breathing, blood constituent change due to a meal, changes in hydration, changes in posture, and changes of blood vessel diameter under parasympathetic nerve and endocrine control.

TABLE 12

Pulse Averaged Value and Pulse Averaged Slope for In Vivo Measurements through a Finger

| Reading | Pulse Averaged Value Recording channel | | | Pulse Averaged Slope Recording channel | | |
| --- | --- | --- | --- | --- | --- | --- |
| | A | B | C | A | B | C |
| 1 | 173834.8 | 201377.1 | 109716.8 | 798.7 | 685.1 | 348.6 |
| 2 | 129694.2 | 155202.5 | 94096.6 | 2601.0 | 2244.8 | 958.6 |
| 3 | 165658.2 | 193309.0 | 108043.4 | 1053.1 | 917.2 | 468.2 |
| 4 | 134148.8 | 160299.9 | 96947.5 | 2715.1 | 2358.6 | 1028.1 |
| 5 | 177710.9 | 207105.9 | 115623.2 | 638.2 | 548.6 | 306.8 |
| 6 | 147823.6 | 175407.4 | 103424.5 | 1855.2 | 1612.2 | 718.1 |

Note: Odd number readings were recorded with subject in the sitting position while even number readings were recorded with subject in the standing position.

TABLE 13

Statistical Analysis of the Results in Table 12

| Position | | Pulse Average Value Recording channel | | | Pulse Averaged Slope Recording channel | | |
| --- | --- | --- | --- | --- | --- | --- | --- |
| | | A | B | C | A | B | C |
| Sitting | Average | 172401.3 | 200597.3 | 111127.8 | 830.0 | 717.0 | 374.5 |
| | Std. Dev. | 6152.9 | 6931.4 | 3982.0 | 209.2 | 186.4 | 83.8 |
| | CV (%) | 3.57% | 3.46% | 3.58% | 25.21% | 25.99% | 22.37% |
| Standing | Average | 137222.2 | 163636.6 | 98156.2 | 2390.4 | 2071.9 | 901.6 |
| | Std. Dev. | 9447.4 | 10507.6 | 4780.0 | 467.0 | 402.1 | 162.7 |
| | CV (%) | 6.88% | 6.42% | 4.87% | 19.54% | 19.41% | 18.04% |

TABLE 14

Normalization and Scaling of Results in Table 12

| Reading | Ratio of Pulse Averaged Value Recording channel | | | Ratio of pulse Averaged Slope Recording channel | | |
| --- | --- | --- | --- | --- | --- | --- |
| | A | B | C | A | B | C |
| 1 | 86323.0 | 100000.0 | 54483.3 | 116581.5 | 100000.0 | 50883.1 |
| 2 | 83564.5 | 100000.0 | 60628.3 | 115867.8 | 100000.0 | 42703.1 |
| 3 | 85696.1 | 100000.0 | 55891.6 | 114816.8 | 100000.0 | 51046.7 |
| 4 | 83686.1 | 100000.0 | 60478.8 | 115114.9 | 100000.0 | 43589.4 |
| 5 | 85806.8 | 100000.0 | 55828.1 | 116332.5 | 100000.0 | 55924.2 |
| 6 | 84274.4 | 100000.0 | 58962.4 | 115072.6 | 100000.0 | 44541.6 |

Note: Odd number readings were recorded with subject in the sitting position while even number readings were recorded with subject in the standing position.

TABLE 15

Statistical Analysis of the Results in Table 14

| Position | | Ratio of Pulse Averaged Value Recording channel | | | Ratio of pulse Averaged Slope Recording channel | | |
|---|---|---|---|---|---|---|---|
| | | A | B | C | A | B | C |
| Sitting | Average | 85942.0 | 100000.0 | 55401.0 | 115910 | 100000 | 52618 |
| | Std. Dev. | 334.6 | 0.0 | 795.4 | 955.1 | 0.0 | 2864.4 |
| | CV (%) | 0.39% | 0.00% | 1.44% | 0.82% | 0.00% | 5.44% |
| Standing | Average | 83841.7 | 100000.0 | 60023.2 | 115351 | 100000 | 43611 |
| | Std. Dev. | 379.7 | 0.0 | 921.7 | 447.4 | 0.0 | 919.4 |
| | CV (%) | 0.45% | 0.00% | 1.54% | 0.39% | 0.00% | 2.11% |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An apparatus for determining the concentration of an analyte of interest within the body of a mammal comprising;
   (a) at least one source of light, said at least one source of light capable of generating electromagnetic radiation at a plurality of wavelengths;
   (b) means for transmitting said radiation into a body part, said transmitting means comprising at least one measurement channel and at least one reference channel;
   (c) means for concurrently measuring radiation that has emerged from said body part;
   (d) means for normalizing the measurement of radiation from said at least one measurement channel to said at least one reference channel so that noise common to said at least one measurement channel and said at least one reference channel is removed; and
   (e) means for processing data to convert said normalized measurement to the concentration of said analyte.

2. The apparatus of claim 1, wherein said at least one source of light is capable of providing light having wavelengths ranging from about 750 nm to about 2500 nm.

3. The apparatus of claim 1, wherein said analyte of interest is selected from the group consisting of glucose, urea, creatinine, ketone, bilirubin, hemoglobin, urobilinogen, and protein.

4. The apparatus of claim 1, wherein said at least one measurement channel comprises at least two measurement channels.

5. The apparatus of claim 1, wherein said at least one measurement channel comprises from two channels to seven channels.

6. The apparatus of claim 1, said means for transmitting said radiation further comprising at least one rotating filter wheel.

7. The apparatus of claim 1, said means for transmitting said radiation further comprising at least one beam splitter.

8. The apparatus of claim 1, said means for concurrently measuring radiation further comprising at least one detector.

9. The apparatus of claim 1, further comprising a means for causing blood to become engorged in an area where said light is transmitted.

10. The apparatus of claim 1, further comprising a means for calibrating said apparatus with known reference values of said analyte of interest.

11. A method for determining the concentration of an analyte of interest within the body of a mammal comprising;
   (a) generating electromagnetic radiation at a plurality of wavelengths, said wavelengths being selected so that at least one of said wavelength is used for measurement of said analyte and at least one of said wavelengths is used for reference, said wavelengths not overlapping;
   (b) transmitting said electromagnetic radiation into a body part;
   (c) concurrently measuring electromagnetic radiation that has emerged from said body part;
   (d) normalizing the radiation measured at the wavelength used for measurement to the radiation used for reference to remove noise that is common to both said measurement radiation and said reference radiation, thereby generating a noise reduced measurement;
   (e) converting said noise reduced measurement to the concentration of said analyte of interest.

12. The method of claim 11, wherein said electromagnetic radiation has wavelengths ranging from about 750 nm to about 2500 nm.

13. The method of claim 11, wherein said analyte of interest is selected from the group consisting of glucose, urea, creatinine, ketone, bilirubin, hemoglobin, urobilinogen, and protein.

14. The method of claim 11, wherein said step of concurrently measuring is verified by the criteria that the peak value of the cross correlation function of a segment of reference measurement to a measurement reference is greater than 0.5, the size of segment being equivalent to data points covered in a heartbeat pulse.

15. The method of claim 11, wherein said step of concurrently measuring is verified by the criteria that the peak value of the cross correlation function of a segment of reference measurement to a measurement reference is at least 0.90, the size of segment being equivalent to data points covered in a heartbeat pulse.

16. The method of claim 11, wherein said normalizing step involves determining the ratio of said at least one measurement reading to said at least one reference reading.

17. The method of claim 11, further including the step of increasing the amount of blood in the area where radiation is transmitted.

18. The method of claim 17, wherein said step of increasing the amount of blood is carried out by applying heat or vacuum to the surface of skin where radiation is transmitted.

19. The methods of claim 11, wherein the data of said measurement and said reference have been preprocessed by calculating slope of the heartbeat before said normalizing step.

20. The method of claim 11, further including the step of using a multivariate analysis method to relate the noise reduced signals to the known value of the analyte of interest.

21. The method of claim 20, wherein said multivariate analysis method is selected from the group consisting of classical least squares, partial least squares, principle component analysis, and neural networks.

* * * * *